US010568962B2

(12) United States Patent
Gabriele et al.

(10) Patent No.: US 10,568,962 B2
(45) Date of Patent: Feb. 25, 2020

(54) HYPERTHERMIA TARGETING COMPOSITIONS, DEVICES, AND METHODS FOR CANCER THERAPY

(71) Applicant: THE SECANT GROUP, LLC, Telford, PA (US)

(72) Inventors: Peter D. Gabriele, Frisco, TX (US); Jared Ely, Quakertown, PA (US); Jeremy J. Harris, Doylestown, PA (US)

(73) Assignee: THE SECANT GROUP, LLC, Telford, PA (US)

( * ) Notice: Subject to any disclaimer, the term of this patent is extended or adjusted under 35 U.S.C. 154(b) by 630 days.

(21) Appl. No.: 15/171,124

(22) Filed: Jun. 2, 2016

(65) Prior Publication Data

US 2016/0354466 A1   Dec. 8, 2016

Related U.S. Application Data

(60) Provisional application No. 62/169,694, filed on Jun. 2, 2015.

(51) Int. Cl.
*A61K 41/00* (2020.01)
*A61N 1/40* (2006.01)
(Continued)

(52) U.S. Cl.
CPC .......... *A61K 41/0052* (2013.01); *A61K 47/34* (2013.01); *A61N 1/403* (2013.01);
(Continued)

(58) Field of Classification Search
CPC .... A61K 41/0052; A61K 47/34; A61N 1/403; A61N 5/025; C08G 63/12; C08G 63/914
See application file for complete search history.

(56) References Cited

U.S. PATENT DOCUMENTS

| 4,632,964 A | 12/1986 | Altschuler et al. |
| 8,541,029 B2 * | 9/2013 | Gabriele ............... A61K 9/0009 424/130.1 |
| 2013/0140649 A1 * | 6/2013 | Rogers ................... H01L 29/66 257/414 |

OTHER PUBLICATIONS

Ranjana, et al. Synthesis, properties and biomedical applications of poly(glycerol sebacate) (PGS): A review, Progress in Polymer Science, Pergamon Press, Oxford, GB, vol. 37, No. 8, (Jan. 27, 2012) pp. 1051-1078, XP028497282, ISSN: 0079-6700, DOI: 10.1016/j.progpolymsci.2012.02.001.

(Continued)

*Primary Examiner* — Kaitlyn E Smith
*Assistant Examiner* — Tigist S Demie
(74) *Attorney, Agent, or Firm* — McNees Wallace & Nurick LLC (57) ABSTRACT

A method of cancer hyperthermia therapy includes placing a device including an exogenously-excitable polymeric material at a cancer hyperthermia therapy site of a patient. The method also includes supplying an exogenous energy to the device such that the exogenous energy excites the exogenously-excitable polymeric material at the cancer hyperthermia therapy site to heat the cancer hyperthermia therapy site to a hyperthermia temperature. A method of preparing a polymeric material includes combining an alcohol monomer, a seed of the polymeric material, and an aqueous liquid in a vessel. The method also includes adding an acid monomer to the vessel and supplying an exogenous energy to the vessel. The polymeric material is exogenously excited by the exogenous energy to heat the polymeric material. The method further includes removing water from the vessel and producing the polymeric material, which is a polyester, in the vessel.

17 Claims, 1 Drawing Sheet

(51) Int. Cl.
 *A61N 5/02* (2006.01)
 *A61K 47/34* (2017.01)
 *C08G 63/12* (2006.01)
 *C08G 63/91* (2006.01)
(52) U.S. Cl.
 CPC ............. *A61N 5/025* (2013.01); *C08G 63/12* (2013.01); *C08G 63/914* (2013.01)

(56) References Cited

OTHER PUBLICATIONS

Jaafar, et al. Spectroscopic evaluation, thermal, and thermomechanical characterization of poly(glycerol-sebacate) with variations in curing temperatures and durations, Journal of Materials Science, Kluwer Academic Publishers, BO, vol. 45, No. 9, (Feb. 4, 2010), pp. 2525-2529, XP019790831, ISSN: 1573-4803.

Li, et al. Criteria for Quick and Consistent Synthesis of Poly(glycerol sebacate) for Tailored Mechanical Properties, Biomacromolecules, vol. 16, No. 5, (May 11, 2015), pp. 1525-1533, XP055326722, US ISSN: 1525-7797, DOI: 10.1021/acs.biomac.5b00018.

* cited by examiner

HYPERTHERMIA TARGETING COMPOSITIONS, DEVICES, AND METHODS FOR CANCER THERAPY

CROSS-REFERENCE TO RELATED APPLICATIONS

This application claims priority to and the benefit of U.S. Provisional Application No. 62/169,694 filed Jun. 2, 2015, which is hereby incorporated by reference in its entirety herein.

FIELD OF THE INVENTION

The present disclosure is generally directed to articles and methods for delivering therapeutic and/or diagnostic materials and methods of making such materials. The present disclosure is more particularly to articles and methods for focused therapy of pharmaceuticals or other therapeutic materials and/or diagnostic materials to humans and other living organisms and methods of making such materials.

BACKGROUND OF THE INVENTION

Many diseases, such as cancer, are often pernicious and very aggressive. Treatment is often complicated by the fact that some of the most effective treatment methods can have a deleterious impact on surrounding healthy tissue and cells. As a result, more recent efforts have moved toward therapies which attempt to target only unhealthy cells and thereby minimize the impact on healthy cells.

Hyperthermia is one such approach to cancer therapy. Hyperthermia associated with radiotherapy or chemotherapy is a method for cancer treatment in which body tissue is exposed to high temperatures, up to 113° F. (45° C.). Although the molecular mechanisms of this process are not well understood, hyperthermia exhibits various anti-tumor effects, including damage of tumor cell structure and vasculature. Research has shown that high temperatures can damage and kill cancer cells, usually with minimal injury to normal tissues. By killing cancer cells and damaging proteins and structures within cancer cells, hyperthermia may shrink tumors.

Hyperthermia is almost always used with other forms of cancer therapy, such as radiation therapy and chemotherapy. Hyperthermia may make some cancer cells more sensitive to radiation or harm other cancer cells that radiation cannot damage. When hyperthermia and radiation therapy are combined, they are often given within an hour of each other. Hyperthermia may also enhance the effects of certain anticancer drugs.

Numerous clinical trials have studied hyperthermia in combination with radiation therapy and/or chemotherapy. These studies have focused on the treatment of many types of cancer, including sarcoma, melanoma, and cancers of the head and neck, brain, lung, esophagus, breast, bladder, rectum, liver, appendix, cervix, and peritoneal lining (mesothelioma). Many of these studies, but not all, have shown a significant reduction in tumor size when hyperthermia is combined with other treatments. However, not all of these studies have shown increased survival in patients receiving the combined treatments.

In local hyperthermia, heat is applied to a small area, such as a tumor, using various techniques that deliver energy to heat the tumor. Different types of energy may be used to apply heat, including microwave, radio-frequency, and ultrasound energy. Depending on the tumor location, there are several approaches to local hyperthermia.

External approaches are used to treat tumors that are located in or just below the skin. External applicators are positioned around or near the appropriate region, and energy is focused on the tumor to raise its temperature.

Intraluminal or endocavitary methods may be used to treat tumors within or near body cavities, such as the esophagus or rectum. Probes are placed inside the cavity and inserted into the tumor to deliver energy and thereby heat the area directly.

Interstitial techniques are used to treat tumors deep within the body, such as brain tumors. These techniques allow the tumor to be heated to higher temperatures than external techniques. Under anesthesia, probes or needles are inserted into the tumor. Imaging techniques, such as ultrasound, may be used to make sure the probe is properly positioned within the tumor. The heat source is then inserted into the probe. Radiofrequency ablation (RFA) is a type of interstitial hyperthermia that uses radio waves to heat and kill cancer cells.

In regional hyperthermia, various approaches may be used to heat large areas of tissue, such as a body cavity, organ, or limb.

Deep tissue approaches may be used to treat cancers within the body, such as cervical or bladder cancer. External applicators are positioned around the body cavity or organ to be treated, and microwave or radiofrequency (RF) energy is focused on the area to raise its temperature.

Regional perfusion techniques may be used to treat cancers in the arms and legs, such as melanoma, or cancer in some organs, such as the liver or lung. In this procedure, some of the patient's blood is removed, heated, and then pumped (perfused) back into the limb or organ. Anticancer drugs are commonly given during this treatment.

Continuous hyperthermic peritoneal perfusion (CHPP) is a technique used to treat cancers within the peritoneal cavity (the space within the abdomen that contains the intestines, stomach, and liver), including primary peritoneal mesothelioma and stomach cancer. During surgery, heated anticancer drugs flow from a warming device through the peritoneal cavity. The peritoneal cavity temperature typically reaches about 106-108° F. (about 41.1-42.2° C.).

Whole-body hyperthermia is used to treat metastatic cancer that has spread throughout the body. This may be accomplished by several techniques that typically raise the body temperature to about 107-108° F. (about 41.7-42.2° C.), including the use of thermal chambers (similar to large incubators) or hot water blankets.

Cancer cells are more sensitive to higher body temperatures than are normal cells. Hyperthermia destroys cancer cells by raising the tumor temperature to a "high fever" range, similar to the way the body uses fever naturally when combating other forms of disease. Because the body's means of dissipating heat is through cooling from blood circulation, sluggish or irregular blood flow leaves cancerous tumor cells vulnerable to destruction at elevated temperatures that are safe for surrounding healthy tissues with normal, efficient blood cooling systems.

Although not wishing to be bound by theory, scientists tend to attribute the destruction of cancer cells at hyperthermic temperatures to damage in the plasma membrane, the cytoskeleton, and the cell nucleus. Cancer cells are vulnerable to hyperthermia therapy particularly due to their high acidity caused by the inability to properly expel waste created by anaerobic metabolism. Hyperthermia attacks acidic cells, disrupting the stability of cellular proteins and killing them.

Radiofrequency hyperthermia is a non-ionizing form of radiation therapy that can substantially improve results from cancer treatment. For chemotherapy drugs that depend on blood transport for delivery, hyperthermia used in combination with chemotherapy (thermo-chemotherapy) enhances blood flow in tumor tissues, increasing the uptake of chemotherapy drugs in tumor membranes. Hyperthermia also induces disassembly of the cytoskeleton, which enlarges the tumor pores for easier drug entry. Once the drug is delivered, hyperthermic temperatures may be used as a drug activator, accelerating chemical reactions through heat and drawing essential oxygen molecules to tumor tissue for chemical reaction with the drug.

Several therapies are associated with non-ionizing RF hyperthermic therapy. One is RF ablation, where direct radio-stimulation contact of cancerous tissues creates a local heat intense enough to kill neoplastic cells. Another RF approach is to direct RF at nanoparticle and microparticle targets localized in the tumor site. These nano and micro spheres may be affixed with antibodies to focus the delivery of the particle to the tumor site that then becomes the target of RF stimulation to directly deliver heat to the local tissue. Still another approach is to combine the separate actions of chemotherapeutic agents with tissue hyperthermia.

Polymers are used extensively in the preparation of biomaterials. Certain biomaterials used in the field include biocompatible and/or bioabsorbable synthetic polymers that are composed of monomers having different affinities for water. For example, in certain polymers formed from glycerol and a diacid, the glycerol may be water soluble while the diacid is nearly insoluble. Thus, when biomaterials including these compounds are prepared, the process for such preparation may simply include adding the monomers neatly to a vessel and allowing them to react directly. Such processes may be problematic because the polymerization reaction may be difficult to control and modify. The products of such reactions may have inconsistent properties between batches, resulting in biomaterials that may fail to perform consistently.

A conventional process of forming poly(glycerol sebacate) (PGS) via an anhydrous polycondensation reaction includes reacting glycerol and sebacic acid at about 248° F. (about 120° C.) for about 24 hours followed by about 48 hours at about 248° F. (about 120° C.) and a pressure of about 1 Torr or less to yield a colorless elastomer. The length of time for this synthesis and the high polydispersity of the PGS product limit the commercial viability of the PGS product.

BRIEF DESCRIPTION OF THE INVENTION

In an embodiment, a method of cancer hyperthermia therapy includes placing a device including an exogenously-excitable polymeric material at a cancer hyperthermia therapy site of a patient. The method also includes supplying an exogenous energy to the device such that the exogenous energy excites the exogenously-excitable polymeric material at the cancer hyperthermia therapy site to heat the cancer hyperthermia therapy site to a hyperthermia temperature.

In another embodiment, a device for cancer hyperthermia therapy by exogenous energy includes an exogenously-excitable polymeric material.

In yet another embodiment, a method of preparing a polymeric material includes combining an alcohol monomer, a seed of the polymeric material, and an aqueous liquid in a vessel. The method also includes adding an acid monomer to the vessel and supplying an exogenous energy to the vessel. The polymeric material is exogenously excited by the exogenous energy to heat the polymeric material. The method further includes removing water from the vessel and producing the polymeric material from the vessel. The polymeric material includes a polyester of the alcohol monomer and the acid monomer.

Other features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Provided are articles and methods for focused therapy of pharmaceuticals or other therapeutic materials and/or diagnostic materials to humans and other living organisms and methods of making such materials.

Embodiments of the present disclosure, for example, in comparison to concepts failing to include one or more of the features disclosed herein, selectively deliver a therapeutic material, which may, for example, be used for selective attack of cancer cells; selectively deliver a diagnostic material, which may, for example, be used for identifying cancer cells; combine two components that would otherwise impose compositional difficulties into the same structure, for example multiple wafer composite compositions to release, for example, a pro-drug component into the necrotic space following hyperthermia to combine for continued therapy; diminish the effect of an active pharmaceutical ingredient on matrix degradation and diffusion activity, where additional heat may act as a kinetic pump to overcome free energy equilibrium; control diffusion of therapeutic and/or diagnostic material in conjunction with the release of material in response to an exogenous stimulus; raise the site of hyperthermia therapy to a hyperthermia temperature essentially by excitation of an exogenously-excitable polymeric material by exogenous energy; or a combination thereof.

The combination of hyperthermia and chemotherapy may be synergistic. Selection of materials and textile design may enhance synergistic behavior. Likewise, textile forming design may be an advantage. It will be appreciated that references to textile forming is not limited to the connotation of cloth, but rather the engineering ability to create three-dimensional (3-D) structures.

Figure 1:
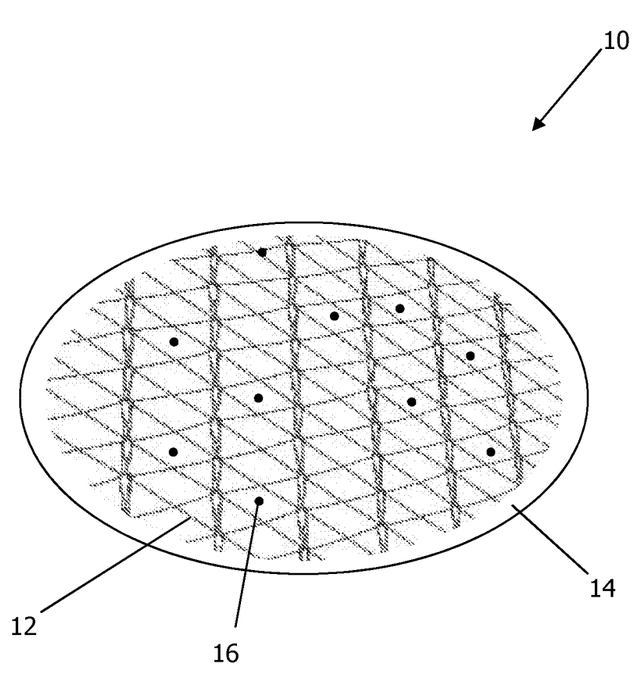
FIG. 1 is a schematic view of a device in an embodiment of the present disclosure.

FIG. 1 schematically shows a device 10 including a textile mesh construct 12, an exogenously-excitable polymeric material 14, and an active load 16, which may be an active pharmaceutical ingredient API. At least a portion of the textile mesh construct 12 is imbedded in the exogenously-excitable polymeric material 14, and the textile mesh construct 12 is deployable and retrievable following therapeutic exposure. The active pharmaceutical ingredient is dispersed within the exogenously-excitable polymeric material 14.

In some embodiments, the compositions and devices are used in local, regional, and/or whole-body hyperthermia methods. Each area may require a customizing of the basic concepts herein to address specific body regions. In some embodiments, the compositions and devices are designed as a pad or patch to cover one or more regions of interest. In some embodiments, the compositions and devices allow for interstitial placement within the tumor tissue. In some embodiments, a larger version of an "antennae blanket" may be used to encase an entire organ or a specific tumor for treatment. A benefit of poly(glycerol sebacate) (PGS) may be to eliminate adhesions and reduce the immune system response. In some embodiments, the compositions and devices are designed to optimize those factors that are antagonistic to neoplastic growth.

In some embodiments, a device 10 is a composite that includes a textile mesh construct 12 such as a fine knitted gold structure mesh (such as the structures used in gold mesh satellite antennas) and a bioresorbable resin, such as PGS, as the excitable material 14. In other embodiments, the device 10 includes a textile mesh that is itself formed of PGS or other exogenously excitable polymeric material 14.

The fine structure is preferably of a dimension to permit formation of a minimally-invasive deployable device 10 through a lumen, much like hernia mesh is deployed during laparoscopic surgery, that serves as a targeting device 10 in radiofrequency (RF) hyperthermia.

In some embodiments, such a structure is combined with a bioresorbable resin, such as, for example, PGS, to construct a deployable mesh-resin-active "wafer", a composite article that may be inserted into a solid tumor for RF exposure treatment.

Such a composite structure may include an inert metallic fine textile, which may be knitted, braided, woven, or non-woven, in gold, a gold alloy, or a biodegradable metal capable of generating heat when exposed to RF hyperthermia frequencies. The composite structure may also include a bioresorbable resin, such as, for example, PGS, or a combination of bioresorbable resins, an active pharmaceutical agent, a modifying agent, a biological, and/or any suitable therapeutic or bioprocessable material.

The composite mesh wafer may be further constructed into a composite structure whereby the textile mesh construct 12 is sandwiched between polymer layers or coatings of bioresorbable polymers. In some embodiments, other geometric forms may be considered. A beneficial feature for using PGS polymer is to minimize immune response during therapy. The circular wafer construct may not be the only geometrical shape, as, for instance, using a braided design creates rods, tube, or needle-like structures for different modes of penetration. Cylinders and spheres are also possible. Furthermore, a knit braid structure may provide a hollow lumen that may contain other agents, such as an API.

In some embodiments, the textile component includes 0.001" (25 μm) gold warp knit on a fully-threaded 20-gauge tricot machine using two bars with a 1-0/1-2 pattern on the first bar and a 1-2/1-0 pattern on the second bar, although other appropriate patterns may be used within the spirit of the present invention.

In some embodiments, the knit is constructed on a Lamb circular warp knitter using a similar pattern, but in a tubular format.

In some embodiments, a 0.001" (25 μm) gold-braided structure is created on a 48-carrier braider, which is then formed into a disc shape by pushing the distal end towards the proximal end to foreshorten the braid.

In some embodiments, a 0.001" (25 μm) gold mesh is woven in a balanced porous plain weave structure to create a receptive grid.

In some embodiments, the wafer includes an RF-responsive polymer, free of a metallic mesh, in which heat sufficient to result in hyperthermic treatments is achieved by RF energy absorbed by the polymer wafer alone, which, like the composites, may include one or more APIs or other modifiers.

In some embodiments, the textile mesh construct 12 may include fiber wire, such as gold mesh antennae structures constructed, intermingled, or interlaced by knitting, braiding, or weaving or non-woven compression of short fiber lengths further constructed into a composite article. It should be noted that the textile mesh construct 12 may include ultrafine gold or other element-based metallic wire, which is considered a synonymous term with fiber wire, fiber in the textile engineering context. In some embodiments, the textile mesh construct 12 of a mesh composite article includes gold wire deep space telecommunication antennae mesh such as that used in orbital radio communication, whereby the construction of the mesh pores (increasing density of the interlacement positions of metal fiber resulting from the interlacement) may be manipulated or designed to increase or decrease pore density to enhance or modulate RF capture.

In aerospace use, the antennae receive RF signals of various RF frequencies. In some embodiments, such a gold or metallic textile mesh structure 12 is further developed as an implantable device 10 composite article with a bioresorbable polymer and an active pharmaceutical ingredient or biologic agent that act as "embedded RF antennae" to capture RF energy to heat up during hyperthermia therapy. In some embodiments, methods deploy the composite article mesh structure into a tumor through a cannula or trocar in a minimally invasive fashion. In some embodiments, the composite article is placed directly into the patient by a surgical technique.

A benefit of the pore shape may be related to target node density, leading to heat transfer focus and efficiency of energy absorption and transfer. The pore size may also be a functional space for resin base reinforcement of the structure or placement of additional therapeutic agents. In addition, the pore space may be the domain into which a secondary therapeutic is combined and embedded, such as, for example, particle therapy for the combined release of microparticle or nanoparticle hyperthermia devices in conjunction with the mesh composite article.

In some embodiments, methods include stent coating of this textile mesh construct 12 or embedding the mesh composite article with or into a bioresorbable resin formulation containing modifiers, including microparticles and/or nanoparticles from traditional particle hyperthermia treatment, chemotherapeutic agents, as well as other effective APIs, and excipient materials, creating a coated mesh wafer, which may be one of a variety of sizes. Furthermore, the mesh wafer may be laminated between bioresorbable films to form a laminate mesh wafer. This is especially attractive when the microparticle therapy is also resorbable.

One of the limitations of finite non-resorbable particle therapy is the fact that these particles remain in the necrotic tissue zone following RF exposure. With every subsequent RF exposure, the residual particles generate heat and run the risk of killing newly-regenerated healthy tissue along with killing cancer cells. Therefore, another advantage of resorbable particles is the ability to retrieve the entire textile mesh construct 12 following RF exposure. In the case of using bioresorbable metal for the mesh wire, the textile mesh construct 12 degrades. The device 10 may be deployed and retrieved or, in the case of bioresorbable metals, allowed to be resorbed from the tumor treatment site following use.

In some embodiments, the textile mesh may serve as a bag to encase microparticles as described above to ease and promote the removal of the microparticles post-treatment. The microparticles may include PGS or PGS with additional chemotherapeutic agents, APIs, or other therapeutic agents. The size of the microparticles enhances the release rate as a result of the increased surface area per unit volume. Microparticle delivery within a textile mesh construct allows for non-invasive (i.e. laparoscopic) hyperthermic treatment.

In some embodiments, the mesh wafer is deployed directly into the tumor tissue through a cannula or needle or trocar. A therapeutic use may resemble the implantation of Gliadel wafer tumor therapy with the added hyperthermia feature.

In some embodiments, a placed device 10, in combination with focused RF electromagnetic radiation delivery through a skull cap placed on the patient, impacts a tumor in an area to be treated, such as by destroying one or more blood vessels to cut off blood supply to the tumor, leading to necrosis of the tumor cells.

In some embodiments, a mesh wafer composite article includes an exogenously-excitable textile micro-mesh metallic structure, including RF-sensitive material arranged within the body of the polymer, a bio-compatible polymer matrix forming a body of the composite structure as a coating or film or extrudate, and an active pharmaceutical load arranged within the resinous body. It should be understood that a construct may include a polymer, a metallic textile mesh construct 12, and an active load 16. In some embodiments, the polymer is not exogenously-excitable. In other embodiments, the polymer is an exogenously-excitable polymeric material 14.

In some embodiments, the bioresorbable polymer is formulated to provide specific controlled release properties. The metallic textile mesh structure 12 may be any RF-sensitive material with biocompatibility amenable to textile formation engineering methods. Alternatively, the RF-sensitive textile-forming material may be a non-metallic RF-absorbing fiber or a fiber composition including RF-sensitive material. In some embodiments, a bioresorbable or synthetic non-resorbable fiber is compounded with super-paramagnetic iron oxide, creating an RF-sensitive fiber. In some embodiments, the RF-sensitivity of an exogenously-excitable polymeric material 14, such as PGS, is enhanced with one or more metal oxides of high dipoles, such as super-paramagnetic iron oxide.

In some embodiments, the fiber stock is compounded with non-metallic RF components as well. In addition to an intended use of the RF-sensitive textile structure to encourage death of cancer cells, such a device 10, appropriately formulated, may act as a healing device 10 that encourages cellular regeneration, for example, in the form of an in vivo medication releasing "heating pad." The polymer of the mesh wafer composite article may be formulated and constructed specifically for controlled release properties and a drug release profile using a bioresorbable chemistry, a biocompatible chemistry, or a biostable chemistry. In some embodiments, the active load 16 is a pharmaceutical, a modifier, an additive, a biologic, or another deliverable entity that contributes to the hyperthermia performance. Furthermore the coating, film, or extrudate may contain nanoparticles, microparticles, and/or macroparticles.

It should also be noted that the specific textile design configuration of the textile mesh structure 12 interlacing, i.e. intersecting, intermingling, or interconnected textile fiber forming units, may be considered as having the potential for optimizing the capture of electromagnetic energy with either the pore density of intermingle density or geometric configuration.

In some embodiments, a discrete exogenously-excitable domain includes an exogenously-excitable material. The exogenously-excitable material is configured to be excited by an exogenous stimulus. The exogenously-excitable composite article is arranged for positioning in a coating, film, or extrudate and is a textile structure. For example, some unique cross-member textile configurations may be more efficient at energy reception than others. The coating, film, or extrudate preferably includes a bio-compatible polymer matrix forming a filler body of the mesh wafer, the exogenously-excitable material being in a discrete domain within the polymer body or a configuration of the textile mesh structure 12 of the mesh or inclusions. The exogenously-excitable material may include a textile mesh construct 12 and/or an exogenously-excitable polymeric material 14.

In some embodiments, a discrete active load 16 domain includes a therapeutic material. The therapeutic material is configured to be released into a living organism. The active load 16 domain is arranged for positioning in the composite article. Domains may be defined by various deposition technologies, such as, for example, print and extrusion dies or islands in the sea-like engineering of extruder equipment, if the article is extruded, or printed, if the composite is formed from film lamination technology. The composite article preferably includes a bio-compatible polymer matrix forming a body of the coating, film, or extrudate, with the active load 16 arranged as a discrete domain within the body.

In some embodiments, a coating, film, or extrudate delivery process includes medically identifying a region for treatment by the active load 16, administering a composite article mesh wafer whereby cells from post-surgical debris may be attracted to the mesh wafer, and applying the exogenous stimulus to the region for treatment, thereby releasing an active load 16 into the region for treatment as a post-surgical procedure following tumor removal. The coating, film, or extrudate preferably includes a bio-compatible polymer matrix forming a body of the wafer or extrudate, an exogenously-excitable material arranged within the body, and the active load 16 arranged within the body.

It may be preferred to incorporate an active hemostatic agent into the wafer mesh to control bleeding resulting from deployment.

In some embodiments, the composite article includes a bio-compatible polymer matrix forming a body of the coating, film, or extrudate, an exogenously-excitable particle material arranged within the body such as the mesh wafer, and an active load 16 arranged within the body. The bio-compatible polymer matrix preferably includes a suitable bioresorbable polymer, which may include, but is not limited to, poly(fatty acid dimer-co-sebacic acid) [poly(FAD-SA)], poly[1,3-bis(p-carboxyphenoxy)propane-co-sebacic anhydride] [poly(CCP-SA)], poly(fumaric-co-sebacic anhydride) [poly(FA-SA)], poly(erucic acid-co-dimersebacic acid) [poly(EAD-SA)], polyglycolide (PGA), poly(lactic acid), polydioxanone (PDO), PGS, poly(caprolactone), poly(hydroxyalconates), poly(propylene fumerate), polyanhydrides, polyacetals, poly(ortho esters), polycarbonates, polyurethanes, copolymers thereof, or a combination thereof.

The exogenous stimulus for the exogenously-excitable material may include, but is not limited to, radiofrequency excitation, microwave excitation, terahertz excitation, mid-infrared excitation, near-infrared excitation, visible excitation, ultraviolet excitation, X-ray irradiation excitation, magnetic excitation, electron beam irradiation excitation, or a combination thereof. The active load 16 preferably has therapeutic properties.

In some embodiments, methods selectively attack cancer cells by administering a composite article having an exogenously-excitable material that may be excited to selectively attack cancer cells while leaving healthy cells intact. For example, some chemotherapeutic agents are inherently RF-excitable, resulting from a strong dipole structure, such as cisplatin.

Wafer composite articles may thus be constructed to include discrete domains with approved excipient materials that contain APIs or a combination of API and inactive or functional domains within the composite article domains. Outside of the domains, the wafer may additionally or alternatively include approved excipient materials which contain API, inactive materials, functional materials, or a combination of API and inactive or functional materials.

In some embodiments, a region for treatment is identified by diagnostic techniques. A wafer composite article containing both a therapeutic and an exogenously excitable material is administered to the region for treatment, or, in some cases, beyond the region for treatment. An exogenous stimulus is then applied to the region of treatment, or, in some cases, beyond the region for treatment, thereby releasing the active load 16 into the region for treatment. This process may decrease the effect on regions not identified for treatment.

In some embodiments, a process maximizes the number of healthy cells left intact while attacking the unhealthy cells. In some embodiments, periodic pulses of the exogenous stimulus are applied while the composite wafer is in situ. In the administration of pain medication, this may replace patient-activated intravenous systems for administering pain medicine by providing the patient with control (or limited control) of a device configured to apply the exogenous stimulus. For example, when the patient pushes a button, the exogenous stimulus is activated, thereby causing pain medicine in the composite structure to be released into the patient's body.

The API, which may be the active load 16, may be any therapeutic material. Active pharmaceutical ingredients may include, but are not limited to, adriamycin/bleomycin/vinblastine/dacarbazine (ABVD), AVICINE, Acetaminophen, Acridine carboxamide, Actinomycin, Alkylating antineoplastic agent, 17-N-Allylamino-17-demethoxygeldanamycin, Aminopterin, Amsacrine, Anthracycline, Antineoplastic, Antineoplaston, Antitumorigenic herbs, 5-Azacytidine, Azathioprine, triplatin tetranitrate (BBR3464), BL22, Biosynthesis of doxorubicin, Biricodar, Bleomycin, Bortezomib, Bryostatin, Busulfan, Calyculin, Camptothecin, Capecitabine, Carboplatin, Chlorambucil, Cisplatin, Cladribine, Clofarabine, Cyclophosphamide, Cytarabine, Dacarbazine, Dasatinib, Daunorubicin, Decitabine, Dichloroacetic acid, Discodermolide, Docetaxel, Doxorubicin, Epirubicin, Epothilone, Estramustine, Etoposide, Exatecan, Exisulind, Ferruginol, Floxuridine, Fludarabine, Fluorouracil, 5-Fluorouricil, Fosfestrol, Fotemustine, Gemcitabine, Hydroxyurea, Idarubicin, Ifosfamide, Imiquimod, Irinotecan, Irofulven, Ixabepilone, Lapatinib, Lenalidomide, Liposomal daunorubicin, Lurtotecan, Mafosfamide, Masoprocol, Mechlorethamine, Melphalan, Mercaptopurine, Methotrexate, Mitomycin, Mitotane, Mitoxantrone, Nelarabine, Nilotinib, Nitrogen mustard, Oxaliplatin, first procaspase activating compound (PAC-1), Paclitaxel, Pawpaw, Pemetrexed, Pentostatin, Pipobroman, Pixantrone, Polyaspirin, Plicamycin, Procarbazine, Proteasome inhibitor, Raltitrexed, Rebeccamycin, SN-38, Salinosporamide A, Satraplatin, Stanford V, Streptozotocin, Swainsonine, Taxane, Tegafur-uracil, Temozolomide, N,N',N''-triethylenethiophosphoramide (ThioTEPA), Tioguanine, Topotecan, Trabectedin, Tretinoin, Tris(2-chloroethyl)amine, Troxacitabine, Uracil mustard, Valrubicin, Vinblastine, Vincristine, Vinorelbine, Vorinostat, Zosuquidar, or a combination thereof.

Other therapeutic materials, including, but not limited to, anti-tumor antibodies, including, for example, vascular endothelial growth factor-A (VEGF-A) or other monoclonal antibodies, antibiotics, bio-agents, bio-pharmaceuticals, and/or other suitable therapeutic materials, may be included. Additionally or alternatively, diagnostic materials, matrix diffusion control materials, and/or other suitable materials may be included.

The exogenously-excitable material is preferably selected to be excited by an exogenous stimulus. Upon receiving the exogenous stimulus, the exogenously-excitable material may be excited. The exogenously-excitable material may be arranged within the domains in the structure or may be mixed within the microfiber matrix. Various therapies may combine exogenously-excitable materials in the microfiber structure along with the API.

In some embodiments, the wafer composite article includes an RF-sensitive additive as the exogenously-excitable material and a degradable polymer as a bio-compatible matrix that may be administered. The exogenously-excitable material may be exogenously excited in situ at the local site of tumor angiogenesis, such as a receptor-specific region in advancing vascular tissue binding VEGF to facilitate localized heating and thereby denaturing angiogenesis factors and/or destroying abnormal cells at the advancing site. Where the API is the active load 16, the excitation may be configured to expedite breakdown of the matrix, thus releasing the pharmaceutical more quickly. In RF-active embodiments, the microfiber matrix may be formulated with a known additive having a known radiofrequency, lambda max or excitation frequency, which can then be exogenously excited. In another approach, the natural RF response of the cell in the absence of a specific radiosensitive additive is determined by a spectroscopic mechanism, such as, for example, nuclear magnetic resonance (NMR), and a tunable RF generator may be used to administer the exogenous non-ionizing radiation.

In some embodiments, the wafer matrix includes a radiosensitive active pharmaceutical drug arranged within a PGS or polylactide/polyglycolide or other suitable biodegradable/resorbable copolymer, as mentioned above, prepared as one of several extrudable components of the composite structure. For example, a second component may include the copolymer and an antibody, a third component may include the copolymer and a chemotherapeutic agent, which may be an API, and a fourth material may be neat copolymer. In some embodiments, the API is 5-fluorouracil (5-FU), doxorubicin, or acetaminophen.

The polymer matrix of the wafer composite article may be any suitable thermoplastic material that is biologically compatible. Suitable bio-compatible matrix materials generally fall into one of two primary categories, diffusive or degradable. In primarily diffusive matrix materials, active load 16 components diffuse from the initial domain, through the matrix, and eventually into the environment (e.g., bloodstream or tissue) over time, the rate of which may be enhanced or retarded through exogenous stimulation, when an exogenously-excitable material is also present. The stimulation may also modify the diffusive profile to increase the amount transmitted. Exemplary diffusive matrix material may include, but are not limited to, poly(FAD-SA), poly(CCP-SA), poly(FA-SA), poly(EAD-SA), polyglycolide (PGA), poly(lactic acid), PDO, PGS, polycaprolactone, poly(hydroxyalconates), poly(propylene fumerate), polyanhydrides, polyacetals, poly(ortho esters), polycarbonates, polyurethanes, copolymers thereof, and combinations thereof, with PGS sold by Secant Medical, Inc. (Perkasie, Pa.) under the tradename Regenerez® or any known biocompatible synthetic resin polymer.

Degradable material breaks down in the body over time, which may be initiated or the rate enhanced, by stimulation in the presence of an exogenously-excitable material. Exemplary degradable polymers include, but are not limited to, poly(FAD-SA), poly(CCP-SA), poly(FA-SA), poly(EAD-SA), polyglycolide (PGA), poly(lactic acid), PDO, PGS, polycaprolactone, poly(hydroxyalconates), poly(propylene fumerate), polyanhydrides, polyacetals, poly(ortho esters), polycarbonates, polyurethanes, copolymers thereof, and PGS-resorbable co-polymers, and combinations thereof. In some embodiments, the wafer has a bio-compatible polymer matrix such as, for example, PGS. In some embodiments, the matrix is vascular-infusible and bio-compatible material that may be administered parenternally or intravenously into a tumor site to deliver a chemotherapeutic agent that is released over time as the matrix breaks down. Such a system may also be coupled with antibody technology.

In some embodiments, a braided structure is converted into a spherical body. Such a configuration may engulf a solid tumor as an RF shell, blanket, or enclosure.

In some embodiments, domains include "immunospecific targeting agents", which permits the wafer composite article to include antibodies as an active load 16 or particle technology that is released from the composite article with antigen-antibody specificity. While embodiments have been described with respect to cancer therapy, it is contemplated that localized delivery of therapeutic materials in accordance with some embodiments would be useful in the treatment of other diseases, conditions, and disorders by providing different compositions of therapeutic materials, by adjusting the wafer size, or by other modifications, all of which are within the scope of the present invention.

Similarly, the composite article may be used for delivering other materials into an animal (including humans) for therapeutic and/or diagnostic purposes. For example, nutrients, vitamins, toxins, poisons, tracers, and/or other components may be included within the domains of the microfiber extrudate to be released upon excitation of the exogenously-excitable material. In some embodiments, toxins may be administered to canines for the purpose of euthanizing. In some embodiments, a harmless dye that is sensitive to gamma radiation may be administered for the purpose of monitoring exposure to gamma radiation.

In a combined biological composite system, the microfiber biometal may deliver a radiofrequency-sensitive body and a chemotherapeutic drug. The matrix may be eliminated by resorption of the biometal following RF excitement. Thus, a single delivery microfiber composite article based on degradable FDA-compliant drug delivery polymers (including but not limiting to poly(FAD-SA), poly(CCP-SA), poly(FA-SA), poly(EAD-SA), polyglycolide (PGA), poly(lactic acid), PDO, PGS, polycaprolactone, poly(hydroxyalconates), poly(propylene fumerate), polyanhydrides, polyacetals, poly(ortho esters), polycarbonates, polyurethanes, copolymers thereof, and combinations thereof), a radiosensitive target material or a radiosensitive chemotherapeutic agent (including, but not limited to, a fluorinated species), a non-radiosensitive chemotherapeutic agent (including, but not limited to, 5-fluorouracil), and an optional antibody (including, but not limited to anti-VEGF antibodies) as separate domains of the structure. In some embodiments, a system includes indigenous acidic properties like those of cancer cells.

In some embodiments, as mentioned above, a stable, multifunctional composite article acting as a nano-carrier may transport superparamagnetic iron oxide nano-particles (SPIONs) and/or nanoparticle domains for simultaneous diagnostic imaging, hyperthermia, or specific therapeutic action, a combination of anti-VEGF antibodies and anti-angiopoietin factors for targeted disruption of angiogenesis, a chemotherapeutic agent, and a microenvironment pH antagonist in a single envelope. Such a microcell may be released from the composite wafer.

In some embodiments, the composite article may be delivered to plants and other living organisms. Some embodiments incorporate ballistic techniques, such as those commonly employed in genetic transformation of crops and other plants for example (e.g., via a gene gun, although the delivery methods described herein are generally not a genetic transformation process per se), to permanently embed the composite articles in plant tissue, which are secured through the use of bio-derived adhesions, such as *Agrobacterium* sp., provided as the discrete domains within the matrix.

In some embodiments, the composite article may be treated to transform its shape and/or geometry. The change in shape and/or geometry may include producing a biomimetic delivery system in the natural range of circulatory cells, transforming the entire shape and/or geometry of the composite article (for example, transforming the matrix of the composite articles), and/or transforming the shape and/or geometry of a portion of the composite article (for example, transforming the domains in the matrix of the composite articles). For example, the composite article may be transformed from a disc-like structure to a sphere-like structure.

In some embodiments, the device 10 may employ a bioresorbable polymer that is itself RF-responsive. One such material is PGS, which has been surprisingly discovered to exhibit responsiveness to RF signals. As a result, PGS may be used in forming a fully bioresorbable, RF controlled release system. Among other advantages, many of the same benefits may be achieved with the composite metallic/polymer composite without fugitive metal remaining in the body.

In still other embodiments, as the following examples also demonstrate, an RF-responsive polymer such as PGS may be used in microwave shielding. For instance, an RF-responsive elastomer may be formulated into a conformal coating that may applied to protect a target, such as a circuit board, for example, from stray microwaves. By way of further example, an RF-responsive elastomer may be formed into sheets or other devices to protect a patient from stray microwaves during microwave imaging or surgery.

In some embodiments, the exogenously-excitable polymeric material 14 is a polymer of an alcohol monomer and an acid monomer. In some embodiments, the polymer is a co-polymer, the alcohol monomer is a multi-alcohol monomer and the acid monomer is a multi-acid monomer. In some embodiments, synthesis of the exogenously-excitable polymeric material 14 includes seeding the reaction mixture with the exogenously-excitable polymeric material 14, applying exogenous energy to the reaction mixture to heat the exogenously-excitable polymeric material 14, thereby bringing the reaction mixture up to reaction temperature, and continuing to apply exogenous energy to the reaction mixture to maintain the reaction temperature through completion of the reaction, for exogenous aqueous catalysis and exogenous polymerization.

In some embodiments, the exogenous energy is the only source of external energy provided for heating the reaction. In other embodiments, the reaction mixture is initially brought up to reaction temperature by an external heating source followed by maintenance of the reaction temperature by application of exogenous energy. In other embodiments, exogenous energy and an external heat source are used in tandem to bring the reaction mixture up to reaction temperature and/or to maintain the reaction mixture at a reaction temperature.

In some embodiments, the exogenous energy is microwave energy and the exogenously-excitable polymeric material 14 is a microwave-excitable material. In other embodiments, the exogenous energy is radiofrequency energy and the exogenously-excitable polymeric material 14 is a radiofrequency-excitable material. In some embodiments, the multi-alcohol monomer is glycerol, the multi-acid monomer is sebacic acid, and the exogenously-excitable polymeric material 14 is PGS.

The addition of water to the mixture before heating causes the sebacic acid to liquefy at a much lower temperature, between about 100° C. and 105° C. (about 212° F. and 221° F.). Because the reaction is an ester condensation, and a product of the reaction is water, the reaction does not progress while a substantial amount of water is present in the reaction mixture. As shown below with respect to the synthesis of PGS, water is a reaction product and thus the presence of additional water in a system containing the reactants slows the reaction kinetics.

tube, and the like that are generally known in the art to contain fluids or fluid-like materials and liquids.

The aqueous liquid may be water alone or be a solution of water and one or more water-soluble agents. The inclusion of water soluble agents allows for the incorporation of such agents into the polymeric material itself, where such agents would be difficult or impossible to provide without the inclusion of the water. Any thermally labile, water-soluble agents may be employed. Water-soluble agents may include, but are not limited to, a vitamin, an anti-inflammatory agent, a protein, a protease, an herbicide, an aquarium food source, an anti-mitotic agent, an anti-platelet agent, an anti-coagulant agent, an anti-thrombotic agent, a thrombolytic agent, an enzyme, a chemotherapeutic agent, an antibiotic agent, an immunological adjuvant, a natural product, a scaffolding material, a processing agent, or a combination thereof. Vitamins may be water-soluble or non-water-soluble, including, but not limited to, vitamin B1, vitamin B2, vitamin B3, vitamin B5, vitamin B6, vitamin B7, vitamin B9, vitamin B12, vitamin C, or a combination thereof.

When water-soluble agents are incorporated or utilized, they are provided in the polymeric material at a therapeutically-effective amount and may be employed in pure form or, where such forms exist, in pharmaceutically acceptable salt, ester, or prodrug form. As used herein, the phrase "therapeutically effective amount" of the water-soluble agents means a sufficient amount of the agents as therapeutics in the treatment of a disorder, at a reasonable benefit/risk ratio applicable to any medical treatment.

The step of combining the alcohol monomer, the seed polymeric material, and the aqueous solution may take place at room temperature in the vessel or may include heating of the alcohol monomer and the aqueous solution to a tem- Once the added water is removed from the reaction, such as by distillation, the remaining reactants remain in liquid form and are homogenously mixed, thus allowing the reaction to proceed in a controlled manner. Furthermore, because the amount of water added is known, a more reliable start time for the reaction may be calculated based on the measurement of the amount of water removed by distillation. That is, once the water initially added is removed, any additional water thereafter removed is water resulting as a product of the reaction.

In some embodiments, the method first includes the step of combining an alcohol monomer, a seed polymeric material, and an aqueous liquid in a vessel. A selected alcohol monomer, utilized in the polymerization of the polymeric material, the seed polymeric material, and the aqueous solution may be combined or otherwise added together either sequentially or simultaneously into a vessel. As used herein, the term "polymer" or "polymeric" may include a homopolymer, copolymer, terpolymer, cross-linked polymer or the like. Moreover, the term "alcohol monomer," may refer to aliphatic alcohols having one or more hydroxy substituents and may, for example, include polyols having two or more hydroxy substituents. In certain aspects, the alcohol monomer may be glycerol.

As used herein the term "vessel" may refer to a beaker, bottle, canister, flask, bag, receptacle, tank, vat, jar, vial, perature of about 50 to 200° C. The heating may include supplying exogenous energy to the mixture. In certain embodiments, the step of combining the alcohol monomer, the seed polymeric material, and the aqueous solution may include heating the alcohol monomer, the seed polymeric material, and the aqueous solution to a temperature of about 80 to about 150° C. (about 176 to about 302° F.) or, preferably, about 90 to about 110° C. (about 194 to about 230° F.). Additionally, the alcohol monomer, the seed polymeric material, and the aqueous solution after combination may be heated for about 5 minutes to about 240 minutes, or about 30 minutes to about 180 minutes, or for a time sufficient to dissolve or homogenously disperse the alcohol monomer and the seed polymeric material in the aqueous solution.

After the alcohol monomer, the seed polymeric material, and aqueous solution are combined in the vessel, an acid monomer may be added to the vessel and mixed with the alcohol monomer and aqueous solution. The acid monomer may be added neatly (i.e., without being dispersed or dissolved in solvent) to the vessel or may be added as a solution or mixture in a selected solvent. The acid monomer may include acidic compounds having one or more acid substituents including, but not limited to, monoacids, diacids, triacids, tetraacids, and the like. In some embodiments, the acid monomer is a diacid. Such diacids may have the formula [HOOC(CH$_2$)$_n$COOH], wherein n=1-30. The diacid may include malonic acid, succinic acid, glutaric acid, adipic acid, pimelic acid, suberic acid, azelaic acid, or sebacic acid. In some embodiments, the diacid is sebacic acid. In some embodiments, the alcohol monomer, acid monomer, and aqueous solution (e.g., water) may be provided in a molar ratio of about 0.5-5 mol alcohol monomer: 0.5-5 mol acid monomer:0.5-5 mol water, with the alcohol monomer and acid monomer preferably present to achieve a molar equivalent of alcohol and diacid monomers. In some embodiments, sebacic acid, glycerol, and water may be provided in a molar ratio of about 1-2 mol sebacic acid, 1-2 mol glycerol, and 2-5 mol water.

The seed polymeric material may be provided in an amount, by weight, in the range of 5 to 50%, alternatively in the range of 5 to 10%, alternately in the range of 5 to 15%, alternatively in the range of 10 to 15%, alternatively in the range of 5 to 25%, alternatively in the range of 10 to 40%, alternatively in the range of 20 to 30%, alternatively in the range of 40 to 50%, alternatively in the range of 25 to 50%, or any sub-range thereof, of the combined weight of the alcohol monomer, the seed polymeric material, and the acid monomer.

Following addition of an acid monomer to the vessel, the contents of the vessel (e.g., alcohol monomer, seed polymeric material, aqueous solution, and acid monomer) may then be refluxed by heating the vessel, preferably at least in part by exogenous energy. Refluxing the contents of the vessel provides, for example, melting of the acid monomer, where the acid monomer is a solid. Indeed, an exemplary process may begin by adding water and seed polymeric material to the reaction mixture of glycerol and sebacic acid, thereby reducing the mixture's overall viscosity. This allows the mixture to be stirred easily. The water provides efficient heat transfer between reaction vessel walls or the exogenously-heated seed polymeric material and the solid acid monomer (e.g., sebacic acid), allowing the acid monomer to melt quickly and form a dispersion. For example, sebacic acid is slightly soluble in water at room temperature, and this solubility is increased as the temperature increases. The suspension or colloidal mixture interaction further facilitates efficient liquefaction of the solid acid monomer. Moreover, the presence of the water in the mixture impedes the reaction of, for example, glycerol and sebacic acid, thus allowing all reactants to be molten and homogenous before the water is removed and the reaction substantially commences.

The step of refluxing the contents of the vessel may also include providing a condenser to the vessel in order to preserve the volume of solvent (e.g., water) contained within the vessel for a predetermined period of time, such as until the acid monomer is completely liquefied. Refluxing the contents of the vessel may include heating the contents to a temperature of about 50 to 200° C. (about 122 to 392° F.) or about 80 to 150° C. (about 176 to 302° F.), either by a heating source or an exogenous energy source. Preferably, the contents of the vessel are heated to a temperature of about 100 to 140° C. (about 212 to 284° F.). As more exogenously-excitable polymeric material 14 is formed, exogenous energy is more rapidly converted to heat energy. Additionally, the alcohol monomer, seed polymeric material, aqueous solution, and acid monomer may be heated for a selected period of time, which may include a period of about 1 to 336 hours or, more particularly, about 24 to 48 hours. Alternatively, where the acid monomer is a liquid or oil at room temperature, the step of refluxing may be avoided. It will further be appreciated that in some embodiments, the vessel may be pressurized to reach temperatures up to 200° C. (392° F.) or higher to shorten the time under reflux and/or for use in melting diacids that remain solid at high temperatures that could not otherwise be readily achieved. In some embodiments, the method of forming the exogenously-excitable polymeric material 14 is completed within about three hours.

After refluxing the contents of the vessel to achieve melting and thorough mixing of the reactants, the water added to the vessel to render that achievement is removed, such as through distillation or any process known in the art. The seed polymeric material and remaining reactants exist in liquid form and are homogenously mixed, thus allowing the reaction to proceed in a controlled manner, which includes the production of additional water as a reaction by-product. That is, some of the water present in the vessel and subsequently removed is a result of its inclusion in the aqueous solution, while some is present as the byproduct of the condensation reaction. By measuring the amount of water removed, it can be determined when the included water has all been removed, which gives a general idea of when the reaction shifts back toward the production of product, meaning that all reactants come to the reaction at the same time.

The step of distilling the water from the vessel may include heating the vessel to a temperature of about 50 to 200° C. (about 122 to 392° F.) or, particularly, about 80 to 150° C. (about 176 to 302° F.). In a particular aspect, the step of distilling the water from the vessel may include heating the vessel to a temperature of about 110 to 140° C. (about 212 to 284° F.), such as about 115° C. (239° F.), 120° C. (248° F.), 125° C. (257° F.), 130° C. (266° F.), or any temperature or range of temperatures therebetween, although vacuum distillation at lower temperatures is also contemplated. At least a portion of the heating preferably occurs by supplying exogenous energy to the seed polymeric material in the reaction vessel.

Following the distillation of the added water from the vessel, the alcohol and acid monomers readily react and polymerize forming the polymeric material. Thus, the polymeric material is thereby produced directly from the vessel to yield the final product. Typically, producing the polymer material includes two separate steps after the added water is removed involving first heating under an inert gas followed by heating under application of vacuum, in which water of reaction is distilled from the vessel. At least a portion of the heating preferably occurs by supplying exogenous energy to the seed polymeric material and additional generated polymeric material in the reaction vessel. Heating the contents of the vessel in these two steps (inert gas purge and vacuum) may be at the same or different temperatures from one another. The temperature may range from about 50° C. to about 200° C. (about 122 to 392° F.) or, particularly, about 80° C. to about 150° C. (about 176 to 302° F.). In some embodiments, the contents of the vessel may be heated to a temperature of about 100° C. to 140° C. (about 212 to 284° F.), such as about 115° C. to about 135° C. (about 239 to 275° F.), such as about 115° C. (239° F.), 120° C. (248° F.), 125° C. (257° F.), 130° C. (266° F.), 135° C. (275° F.), or any temperature or range of temperatures therebetween.

Regarding the heating of the vessel and/or the contents of the vessel in any of the process steps described herein, the heating of the vessel and/or its contents may be performed by conductive heating, convective heating, radiative heating, or a combination thereof. At least a portion of the heating preferably occurs by supplying exogenous energy to the seed polymeric material and additional generated polymeric material in the reaction vessel. With respect to radiative heating, the vessel and/or its contents may be heated with, for example, microwave radiation, radiofrequency radiation, and/or infrared radiation.

The distillation may occur in conjunction with stirring and/or purging the contents of the vessel by reaction under an inert gas, such as following an initial distillation step after reflux to remove the water added as a processing aide. As used herein, the term "inert gas" may refer to nitrogen, carbon dioxide, a noble gas, or a combination thereof. For example, noble gases may include helium, neon, argon, and the like. In certain aspects, the inert gas is nitrogen. The process may include purging the contents of the vessel with an inert gas at a rate of about 1 mL/min to about 10 L/min, such as while heating in the range of temperatures previously described. Moreover, inert gas purging of the vessel may be provided for a period of about 1 minute to about 48 hours or, more particularly, for about 1 hour to about 24 hours and preferably is conducted at atmospheric pressure, although carrying out this step at higher or lower pressures is contemplated.

Distillation may include heating and/or applying sub-atmospheric pressure to the vessel, and in particular distillation to remove water of reaction following the inert gas purge step of producing takes place through the application of a vacuum. For instance, distilling may include connecting a source of sub-atmospheric pressure to the vessel according to any process known in the art (e.g., a fluidic connection of a peristaltic pump, diaphragm pump, rotary pump, etc.). Sub-atmospheric pressure may be applied to the vessel at a pressure of less than about 760 Torr (0.1 MPa) or, particularly, at a pressure of about 40 mTorr to 50 Torr (5 to 6700 Pa). In another aspect, sub-atmospheric pressure may be applied to the vessel at a pressure of about 5 to 20 Torr (670 to 2700 Pa), such as about 10 Torr (1300 Pa).

Additionally, the sub-atmospheric pressure may be applied to the vessel at a constant pressure for a selected period of time or the sub-atmospheric pressure may be varied during the course of its application. For example, the application of subatmospheric pressure may include a stepwise reduction from a first pressure to a second pressure, such as a first pressure less than about 760 Torr (0.1 MPa) and the second pressure greater than about 40 mTorr (5 Pa), particularly, greater than 1 Torr (130 Pa).

The distillation of water from the vessel may include heating and/or applying sub-atmospheric pressure to the vessel for a selected period of time. For example, the heating and/or application of sub-atmospheric pressure to the vessel may be applied for about 1 hour to 336 hours or, more particularly, about 12 hours to 168 hours. In a particular aspect, the heating and/or application of sub-atmospheric pressure to the vessel may be applied such as about 24, about 25 hours, about 26 hours, about 27 hours, up to about 48 hours, or any time or range of times therebetween.

In another aspect, the reactants (e.g., the alcohol and acid monomers) may be allowed to react under the application of sub-atmospheric pressure in addition to, or instead of, heating the reactants. Indeed, sub-atmospheric pressure may be applied to the vessel at a pressure of less than about 760 Torr (0.1 MPa) or, particularly, at a pressure of about 40 mTorr to 50 Torr (5 to 6700 Pa). In another aspect, sub-atmospheric pressure may be applied to the vessel at a pressure of about 1 to 50 Torr (130 to 6700 Pa), such as 5 to 20 Torr (670 to 2700 Pa), such as about 10 Torr (1300 Pa). The polymerization of the alcohol and acid monomers may continue (with or without heating and/or applying sub-atmospheric pressure) for about 1 hour to 336 hours or, particularly, about 12 hours to 168 hours. In a particular aspect, the polymerization (i.e., production of the polymeric material) may continue for about 24 to 120 hours, including about 24 hours, about 25 hours, about 26 hours, about 27 hours, up to about 48 hours, up to about 76 hours, or any time or range of times therebetween.

Upon completion of the polymerization reaction to produce the polymeric material, the resulting polymeric material, which may be in the form of a moldable, pliable resin, is removed from the vessel and stored as necessary or required. Additionally, completion or progress of the processes may be determined by any means known in the art including, but not limited to, Fourier-transform infrared (FTIR) spectroscopy, differential scanning calorimetry (DCS), size-exclusion chromatography (SEC), thermogravimetric analysis (TGA), liquid chromatography mass spectrometry (LCMS), and/or NMR. Among the advantages are that the resulting product is resin that may be subsequently processed and then cured into any size or shape to any level of cross-linking as may be desired for a particular application or may be used in the resin form without any appreciable cross-linking for use, for example, as a coating.

In some embodiments, the aqueous composition is doped with a salt to increase heating and create an isotonic degradable polymer.

In some embodiments, nanoparticles of a biodegradable metal alloy, such as, for example FeMgZn, are incorporated into the reaction mixture, and hence the finished product, to increase RF-heating of finished material.

In some embodiments, hyperthermia treatments, compositions, and devices are non-immunogenic, resist infection, reduce scarring, and do not inflame the healing tissue.

The RF-sensitivity of PGS may be advantageously used in hyperthermia treatment methods in a number of different way. In some embodiments, the RF sensitivity provides a controlled release drug pump for wound care and cancer hyperthermia. In some embodiments, the RF-sensitive polymer degrades after therapeutic treatment. In some embodiments, the textile mesh construct 12 includes PGS-coated biodegradable metal alloy "fibers" or "needles" serving as tumor insertion antenna-targets, where the PGS minimizes infection and controls erosion of the biodegradable metal needles. In some embodiments, the biodegradable metal needles are also bioresorbable. In some embodiments, a biodegradable PGS-coated biodegradable metal alloy mesh is created of a biodegradable metal alloy woven, knitted, or braided structure as the coated RF mesh antenna-target.

In some embodiments, biodegradable metal alloy nanoparticles coated with chemo/drug-loaded PGS and antibodies anchored on the PGS surface for targeted delivery provide controlled release therapy, and cancer hyperthermia. In some embodiments, biodegradable metal alloy nanoparticles serve as part of an RF embolic device 10 for cancer hyperthermia.

In some embodiments, RF-sensitive PGS films, foams, flours, and treatments serve as RF wound care devices 10 to thermally heat-shock pathogenic bacterial at a wound site or wound bed. In some embodiments, RF-sensitive PGS films, foams, flours, and particulate compositions provide wound care antimicrobial protection and thermal induction of angiogenesis as a non-trophic, wound-dressing heating pad. In some embodiments, increasing the RF-sensitivity of PGS increases antimicrobial action by inducing microbial heat shock plus inherent chemical action through breakdown products. In some embodiments, films of PGS polymer act as RF tissue shields to absorb stray RF during RF ablation and RF hyperthermia procedures.

In some embodiments, the local application of the continuous microwave (CM) energy itself may speed up healing of a septic or an aseptic wound or tumor site in addition to advantages provided by application of the microwave energy to the exogenously-excitable polymeric material 14.

In chronic wound care, the wound bed cells may lack active mitochondrial activity and have poor oxygen utilization. PGS proliferates eukaryotic cell activity, and fatty acid metabolism increases ATP production. An advantage of PGS RF hyperthermia exposure is the killing feature of the cancer cell and the heat shock of prokaryotes (bacteria). Cancer cells are hypoxic and may be reversible to normal cell behavior with stimulation of mitochondrial activity resulting from stimulation of oxidative phosphorylation by fatty acids. In some embodiments, the RF-induced degradation of PGS may induce cancer-wound space healing of the non-cancerous cells. In other words, the PGS RF heating may not only kill cancer cells and bacteria but also accelerates breakdown of products from killing cancer cells and bacteria and feeds new eukaryotes growing in the wound space for cancer and chronic wounds by supporting the oxidative process.

In some embodiments, PGS serves as an RF shield coating for electronics and military applications.

In some embodiments, PGS serves as a food additive for rapid microwave heating and in-can preservation of food.

Example 1

A disc of a pure thermoset PGS and a gold mesh embedded in a thermoset PGS disc were each manufactured and were subjected to RF-frequency radiation by mounting on an acrylic support that was then exposed to microwave radiation at 600 W for 1 minute. It was surprisingly discovered that while the gold mesh composite exhibited higher temperatures over the pure PGS, even the pure PGS reached temperatures in excess of 300° F. (150° C.), significant enough to have melted the acrylic support to which it was attached, despite the acrylic support itself having stayed at no more than room temperature, and high enough to be useful in hyperthermia treatment therapies as contemplated herein.

Further testing and observation of the PGS post-heating showed that despite the large amount of absorbed RF energy (and the corresponding amount of heat it emitted), the PGS did not lose its characteristic elasticity.

Example 2

To determine the difference in capability of microwave-heating between PGS and PGA, cast discs of identical volume of PGS and PGA were formed. PGS was cast by thermosetting RG-300 for 72 hours at 120° C. (248° F.) and 10 Torr (1300 Pa). This was done in a 4 1/16" (103 mm) diameter aluminum pan. A 2 7/8" (73 mm) diameter aluminum pan was used to cut a 2 7/8" (73 mm) disc from the larger sample of PGS. PGA was cast by loading PGA pellets into a 2 7/8" (73 mm) diameter aluminum pan, placing the pan on a hot plate, tenting the pan with aluminum foil and heating/melting the PGA at about 250° C. (480° F.) for about 15 minutes. The pan, both prior to and during heating, was purged with nitrogen gas.

For each experiment, a disc was placed in an open-top microwave-invisible polypropylene (PP) container, which was placed on top of a second open-top microwave-invisible PP container that was inverted and placed on the microwave carousel. A microwave-invisible container was selected in order to prevent or minimize heating of the containers by the microwaves, which would lead to conductive heat transfer from the container to the disc during microwave testing.

Each disc was exposed to a predetermined level of microwave power in a microwave oven for a predetermined period of time in the range of 1 to 5 minutes. The disc was then immediately removed from the microwave and a thermal image map was taken using a thermal imaging camera. A maximum temperature reached by the sample was determined using image analysis software with the thermal imaging camera. Table 1 shows the determined maximum temperature. As a control, a PP container without a disc was also tested, and the maximum temperature of the container was determined and is included in Table 1.

TABLE 1

| Maximum Temperature after Microwaving | | | |
|---|---|---|---|
| Time (min) | PP (° F.) | PGS (° F.) | PGA (° F.) |
| 0 | 83.1 | 82.0 | 86.9 |
| 1 | 85.2 | 245.6 | 90.2 |
| 2 | 91.4 | 366.8 | 102.3 |
| 3 | 98.8 | 386.6 | 105.1 |
| 4 | 107.6 | ND | 114.6 |
| 5 | 114.0 | ND | 121.0 |

Even though there was likely some heating of the discs aside from direct microwave heating (as evidenced by the slightly increasing temperature of the PP container with increasing microwaving times), it is apparent from Table 1 that PGS is extremely microwave-active while PGA is either extremely microwave-insensitive or microwave-invisible. The PGA disc did not heat significantly more than an empty PP container, and indeed did not resolve on the thermal images, indicating that it is basically at the same temperature as the surrounding PP container.

As shown in Table 1, the PP containers did experience some heating. The glass carousel became hot during microwaving and did not cool readily, and it is suspected that this is due to convection from the air in the microwave heated from the glass carousel, and possibly the metal sides of the interior of the microwave oven itself. For consistency, the tests were run with the glass carousel typically at about 110° F. (43° C.) but with an initially cool microwave interior at the start of each test. After three minutes of heating, the PGS disc melted the PP container, so no further time points were tested for PGS. The temperature of the room during the experiments was in the range of 80±2.5° F. with 50±5% relative humidity.

Example 3

Samples of sebacic acid, glycerol, water, and sodium chloride were formed by mixing the reactants using the PolyBlock under heat and mixing while blanketed with nitrogen gas. The following reaction mixtures were created:

Reactor 1: Water Mediated PGS—Sebacic Acid, Glycerol, and Water

Reactor 2: Non-Water Mediated PGS—Sebacic Acid and Glycerol

Reactor 3: Water Mediated PGS+Salt—Sebacic Acid, Glycerol, Water, and NaCl

Reactor 4: Non-Water Mediated PGS+Salt—Sebacic Acid, Glycerol, and NaCl

Each reactor was loaded with components at a typical PGS synthesis ratio (with 0.019 mol of NaCl for Reactor 3 and Reactor 4). A reflux assembly was used in each reactor using a condenser tube with −2° C. (28° F.) ethylene glycol-water flowing through the tube. Nitrogen gas was flowed through each reactor at about one liter per minute so as to prevent oxidation while still being a low enough flow to prevent vapors from escaping the reflux assembly. Components were heated to 160° C. (320° F.) over a period of 12 minutes in order to melt the sebacic acid and then stirred for an additional 30 minutes under the same conditions in order to thoroughly mix the components.

Following the above mixing procedure, a puck of apparently crystalline material was formed. These were broken up and stored in polypropylene jars. 10 g of each sample was loaded into a Pyrex beaker and placed in a microwave on top of an inverted polypropylene jar. These samples were microwaved for 8 minutes total at a power level of "2", with slight breaks every two minutes to take a thermal image of the reaction material to assess temperature evolution. The maximum temperatures are shown in Table 2. Each beaker was immediately returned to the microwave after the image had been taken.

During the first microwave test of the material from Reactor 1, the power level of the microwave was not set to "2", and consequently the default power level of the microwave was used for the microwaving procedure. A second test was performed using the excess material produced from the mixing step at a power level of "2".

TABLE 2

| | Reactor Temperature (in ° F.) after Microwaving | | | | |
|---|---|---|---|---|---|
| Time (min) | Reactor 1 (Default) | Reactor 1 | Reactor 2 | Reactor 3 | Reactor 4 |
| 2 | 390.0 | 221.1 | 264.2 | 299.2 | 237.3 |
| 4 | 440.6 | 303.9 | 407.3 | 370.3 | 343.7 |
| 6 | 489.3 | 332.8 | 368.4 | 372.2 | 367.4 |
| 8 | 524.3 | 334.4 | 357.9 | 367.4 | 380.4 |

In both of the salted samples, the salt was still visibly apparent following the microwaving procedure, suggesting that the salt aggregated and did not dissolve or otherwise thoroughly disperse during the mixing step.

The FTIR spectra indicated that some reaction occurred in the microwave. The peak located at ~1690 cm$^{-1}$ decreased over the 8-minute microwave exposure and the peak located at ~1730 cm$^{-1}$ increased. This represents the reduction of carboxylic acid and formation of the carboxylic acid ester. A reduction of the broad peak at ~3300 cm$^{-1}$ representing the —OH stretch of the carboxylic acid indicates a similar trend. However, the presence of some carboxylic acid after 8 minutes indicates that the reaction had not yet completed.

From the temperature study, it can be seen that the non-water mediated PGS seemed to heat more than the water mediated PGS in the microwave. Additionally, the addition of salt seemed to have little to no effect on the heating of the PGS. This may be because the salt was not dissolved in the sample and thus had no effect on the dipoles present in the PGS.

The sample from Reactor 1 which had been microwaved at a power level of "2" was only slightly waxy and still somewhat crystalline and brittle, but all of the other samples, by feel, had a waxy quality similar to PGS following microwaving. The sample from Reactor 1 that was microwaved at the default microwave power level was fully thermoset after 8 min but was extremely brittle and bubbled due to a rolling boil during the cure.

While the invention has been described with reference to one or more embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A method of cancer hyperthermia therapy comprising:
placing a device comprising an exogenously-excitable polymer at a cancer hyperthermia therapy site of a patient; and
supplying an exogenous energy to the device such that the exogenous energy excites the exogenously-excitable polymer at the cancer hyperthermia therapy site to heat the cancer hyperthermia therapy site to a hyperthermia temperature.

2. The method of claim 1 wherein the device consists essentially of the exogenously-excitable polymer.

3. The method of claim 1, wherein the exogenous energy is selected from the group consisting of microwave energy, radiofrequency energy, and a combination of microwave energy and radiofrequency energy.

4. The method of claim 1, wherein the exogenously-excitable polymer comprises poly(glycerol sebacate).

5. The method of claim 1, wherein the device further comprises a textile mesh construct, wherein at least a portion of the textile mesh construct is imbedded in the exogenously-excitable polymer, and wherein the textile mesh construct is deployable and retrievable following therapeutic exposure.

6. The method of claim 1, wherein the device further comprises at least one active pharmaceutical ingredient dispersed within the exogenously-excitable polymer.

7. The method of claim 6, wherein supplying the exogenous energy releases the active pharmaceutical ingredient in a controlled manner.

8. The method of claim 1, wherein the device consists of the exogenously-excitable polymer and at least one active pharmaceutical ingredient dispersed within the exogenously-excitable polymer.

9. The method of claim 8, wherein the exogenously-excitable polymer is poly(glycerol sebacate).

10. The method of claim 8, wherein the exogenously-excitable polymer is a co-polymer of a multi-alcohol monomer and a multi-acid monomer.

11. A device for cancer hyperthermia therapy by exogenous energy, the device comprising an exogenously-excitable polymer, wherein the device is configured such that the exogenous energy excites the exogenously-excitable polymer at a cancer hyperthermia therapy site of a patient to heat the cancer hyperthermia therapy site to a hyperthermia temperature.

12. The device of claim 11 further comprising a textile mesh construct, wherein at least a portion of the textile mesh construct is imbedded in the exogenously-excitable polymer, and wherein the textile mesh construct is deployable and retrievable following therapeutic exposure.

13. The device of claim 12, wherein the textile mesh construct comprises an electromagnetic antennae mesh.

14. The device of claim 11, wherein the exogenous energy is selected from the group consisting of microwave energy, radiofrequency energy, and a combination of microwave energy and radiofrequency energy.

15. The device of claim 11 wherein the exogenously-excitable polymer comprises poly(glycerol sebacate).

16. The device of claim 11 further comprising at least one active pharmaceutical ingredient dispersed within the exogenously-excitable polymer.

17. The device of claim 11, wherein the exogenously-excitable polymer is poly(glycerol sebacate) and the device consists of the exogenously-excitable polymer and at least one active pharmaceutical ingredient dispersed within the exogenously-excitable polymer.

\* \* \* \* \*